United States Patent [19]

Iyer et al.

[11] Patent Number: 5,750,674

[45] Date of Patent: May 12, 1998

[54] METHODS AND COMPOUNDS FOR THE STEREOSELECTIVE ENRICHMENT OF OLIGONUCLEOTIDE DIASTEREOMERS AND OLIGONUCLEOTIDES THEREBY PRODUCED

[75] Inventors: Radhakrishnan P. Iyer; Dong Yu; Sudhir Agrawal, all of Shrewsbury; Weitian Tan, Framingham, all of Mass.

[73] Assignee: Hybridon, Inc., Cambridge, Mass.

[21] Appl. No.: 448,131

[22] Filed: May 23, 1995

[51] Int. Cl.$^6$ ...................................................... C07H 19/20
[52] U.S. Cl. .................. 536/26.7; 536/26.71; 536/26.72; 536/26.74; 536/26.8; 536/25.3; 536/25.33; 536/25.34
[58] Field of Search ............................... 536/25.3, 25.34, 536/23.1, 26.7, 26.71, 26.72, 26.74, 26.8, 25.33

[56] References Cited

U.S. PATENT DOCUMENTS

| | | |
|---|---|---|
| 4,689,320 | 8/1987 | Kaji . |
| 4,806,463 | 2/1989 | Goodchild et al. . |
| 5,107,065 | 4/1992 | Shewmaker et al. . |
| 5,149,798 | 9/1992 | Agrawal et al. . |
| 5,194,428 | 3/1993 | Agrawal et al. . |
| 5,359,052 | 10/1994 | Stec et al. . |
| 5,506,212 | 4/1996 | Hoke et al. ........................... 514/44 |

FOREIGN PATENT DOCUMENTS

| | | |
|---|---|---|
| 8700724 | 10/1988 | Netherlands . |
| WO 9200091 | 1/1992 | WIPO . |
| WO 9401550 | 1/1994 | WIPO . |
| WO9417091 | 8/1994 | WIPO . |
| WO9509236 | 4/1995 | WIPO . |

OTHER PUBLICATIONS

Agrawal and Goodchild, "Oligodeoxynucleoside Methylphosphonates: Synthesis and Enzymic Degradation." *Tetrahedron Lett.* 28, 3539–3542 (1987).

Agrawal and Iyer, "Modified oligonucleotides as therapeutic and diagnostic agents," *Curr. Op. In Biotech.* 6, 12 (1995).

Agrawal et al., "Oligodeoxynucleoside phosphoramidates and phosphorothioates as inhibitors of human immunodeficiency virus," *Proc. Natl. Acad. Sci USA* 85, 7079–7083 (1988).

Alul et al., "Oxalyl—CPG: a labile support for synthesis of sensitive oligonucleotide derivatives." *Nucleic Acids Research* 19(7), 1527–1532 (1991).

Beaucage and Caruthers, "Deoxynucleoside Phosphoramidites—A New Class of Key Intermediates for Deosypolynucleotide Synthesis," *Tetrahedron Lett.* 22, 1859–1862 (1981).

Bonora, "Large scale, liquid phase synthesis of oligonucleotides by the phosphoramidite approach," *Nucl. Acids Res.* 21, 1213–1217 (1993).

Buck et al., "Phosphate–Methylated DNA Aimed at HIV–1 RNA Loops and Integrated DNA Inhibits Viral Infectivity," *Science* 248, 208–212 (1990).

Bukh et al., "Sequence analysis of the 5' noncoding region of hepatitis C virus," Proc. Natl. Acad. Sci. USA 89, 4942–4946 (1992).

Connolly et al., "Synthesis and Characterization of an Octanucleotide Containing the EcoRI Recognition Sequence with a Phosphorothioate Group at the Cleavage Site," *Biochemistry* 23, 3443 (1984).

Debenham J.S. et al., "Two New Orthogonal Amine Protecting Groups That Can Be Cleaved under Mild or Neutral Conditions", *Journal of the American Chemical Society*, vol. 117, No. 11, 22 Mar. 1995, DC US, pp. 3302–3303.

Habus and Agrawal, "Improvement in the synthesis of oligonucleotides of extended length by modification of detritylation step," *Nucl. Acids Res.* 22, 4350–4351 (1994).

Iyer et al., "Improved Procedure for the Reduction of N—1 Content in Synthetic Oligonucleotides," *Nucleosides & Nucleotides* 14, 1349–1357 (1995).

Iyer R.P. et al., "Nucleoside Oxazaphospholidines as Novel Synthons in Oligonucleotide Synthesis", *Journal of Organic Chemistry*, vol. 60, Oct. 1995, Easton US, pp. 5388–5389.

Iyer R.P. et al., "Methyl Phosphotriester Oligonucleotides: Facile Synthesis Using N—Pent—S—enoyl Nucleoside Phosphoramidities", *Journal of Organic Chemistry*, vol. 60, Dec. 1995, Easton US, pp. 8132–8133.

Iyer R.P. et al., "A Novel Phosporamidite Synthon Derived from 1R,2S —Ephedrine", *Tetrahedron : Asymmetry* vol. 6, No., 5, 26 May 1995, Oxford GB, pp. 1051–1054.

Jager et al., "Oligonucleotide N—Alkylphosphoramidates: Synthesis and Binding to Polynucleotides," *Biochemistry* 27, 7237 (1988).

Jones A.S. et al., "Synthesis of some Nucleoside Cyclic Phosphoramidates and Related Compounds via Phosphoramidites", *Journal of the Chemical Society, Perkin Transactions* 1, 1985, Letchworth GB, pp. 199–202.

Khorana et al., "Studies on Polynucleotides," *J. Molec. Biol.* 72,209 (1972).

Koole et al., "A Parallel Right–Handed Duplex of the Hexamer d(TpTpTpTpTpT) with Phosphate Triester Linkages," *J. Am. Chem. Soc.* 109, 3916–3921 (1987).

Koziolkiewicz and Wilk, "Oligodeoxyribonucleotide Phosphotriesters," *Methods in Molecular Biology vol. 20: Protocols for Oligonucleotides and Analogs* pp. 207–220 (Agrawal, Ed., Humana Press, 1993).

(List continued on next page.)

*Primary Examiner*—James O. Wilson
*Attorney, Agent, or Firm*—McDonnell Boehnen Hulbert & Berghoff

[57] ABSTRACT

The present invention provides new mononucleotide synthons useful in the synthesis of oligonucleotides having from one to all P-chiral centers that are predominantly and independently in the R or S configuration. The invention also provides methods of synthesizing these synthons, methods of synthesizing oligonucleotides having from one to all P-chiral centers predominantly and independently in the R or S configuration, and such oligonucleotides. Oligonucleotides synthesized with the novel synthons are useful for modulating nucleic acid expression, both in vitro and in vivo, as well as in traditional hybridization assays.

24 Claims, 1 Drawing Sheet

OTHER PUBLICATIONS

Kraszewski A. et al., "Studies on Reactions of Nucleoside H—Phosphonates with Bifunctional Reagents. Part 1. Reaction with Amino Alcohols", *Journal of the Chemical Society, Perkin Transactions* 1, 1993, Letchworth GB, pp. 1699–1704.

Kuijpers et al., "Synthesis of well-defined phosphate-methylated DNA fragments: the application of potassium carbonate in methanol as deprotecting reagent," *Nucl. Acids Res.* 18, 5197 (1990).

Kumar et al., "Synthesis and Biological Evaluation of Some Cyclic Phosphoramidate Nucleoside Derivatives," *J. Med. Chem. Soc., Chem. Commun.*, 159–161 (1991).

Moody et al., "Inhibition of HIV-1 Infectivity by Phosphate-Methylated DNA: Retraction," *Science* 250, 125–126 (1990).

Moody et al., "Regiospecific inhibition of DNA duplication by antisense phosphate-methylated oligodeoxynucleotides," *Nucleic Acids Research* 17(12), 4769–4782 (1989).

Padmapriya et al., "Large-Scale Synthesis, Purification, and Analysis of Oligodeoxnyucleotide Phosphorothioates," *Antisense Res. Dev.* 4, 185 (1994).

Pon, "Solid-Phase Supports for Oligonucleotide Synthesis," *Methods in Molec. Biol., vol. 20, : Protocols for Oligonucleotides and Analogs*, p. 465–496 (Agrawal, Ed., Humana Press, 1993).

Ravikumar et al., "Synthesis of Oligonucleotides via Phosphoramidite Approach Utilizing 2—Diphenylmethylsilylethyl (DPSE) as a Phosphorus Protecting Group," *Tetrahedron* 50, 9255 (1994).

Reddy et al., "Fast Cleavage and Deprotection of Oligonucleotides," *Tetrahedron Lett.* 35, 4311 (1994).

Reese, "The Chemical Synthesis of Oligo—and Poly—Nucleotides by the Phosphotriester Approach," *Tetrahedron Lett.* 34, 3143–3179 (1978).

Tang et al., "Enzymatic Synthesis of Stereoregular (all Rp) Oligonucleotide Phosphorothioate and its Properties," *Nucleosides Nucleotides*, 14(3–5), 985–900 (1995).

Theisen et al., "N—6—Dialkylformamidine—2'—Deoxyadenosine Phosphoramidites in Oligodeoxynucleotide Synthesis. Rapid Deprotection of Oligodexoynucleotides," *Nucleosides & Nucleotides* 12, 1033 (1993).

Lopez et al., "n–Pentenyl Esters versus n–Pentenyl Glycosides. Synthesis and Reactivity in Glycosidation Reactions," *J. Chem. Soc., Chem. Commun.*, 159–161 (1991).

Zamecnik and Stephenson, *Proc. Natl. Acad. Sci. USA* 75, 280–284 (1978).

Agrawal, *Trends in Biotech.* 10, 152 (1992).

Chang and Pettitt, *Proc. Biophys. Molec. Biol.* 58, 225 (1992).

Uhlmann and Peyman, *Chem. Rev.* 90, 543 (1990).

Stein and Cheng, *Science* 261, 1004 (1993).

Agrawal and Tang, *Antisense Res. and Dev.* 2, 261 (1992).

Bayever et al., *Antisense Res. and Dev.* 3, 383 (1993).

Zon, in *Methods in Molecular Biology*, vol. 20: Protocols for Oligonucleotides and Analogs, pp. 165–189 ( S. Agrawal, Ed., Humana Press, 1993, Totowa, New Jersey).

Zon and Stec, in Oligonucleotides and Analogues: *A Practical Approach*, pp. 87–108 (F. Eckstein, Ed., IRL Press/Oxford University Press, 1991, New York, New York).

Stec and Wilk, *Angew–Chem Int. Ed. Engl.* 33, 709 (1994).

Lesnikowski, *J. Bioorg. Chem.* 21, 127 (1993).

Stec and Lesnikowski, in *Methods in Molecular Biology*, vol. 20: Protocols for Oligonucleotides and Analogs, pp. 285–313 (S. Agrawal, Ed., Humana Press, 1993, Totowa, New Jersey).

Sonveaux, E., in *Methods in Molecular Biology*, vol. 26: Protocols for Oligonucleotide Conjugates, pp. 1–72 (S. Agrawal, Ed., Humana Press, 1994, Totowa, New Jersey).

Meyer, R., in *Methods in Molecular Biology*, vol. 26: Protocols for Oligonucleotide Conjugates, pp. 73–92 (S. Agrawal, Ed., Humana Press, 1994, Totowa New Jersey).

Beaucage, S., in *Methods in Molecular Biology*, vol 20: Protocols for Oligonucleotides and Analogs, pp. 33–61 (S. Agrawal, Ed., Humana Press, 1993, Totowa, New Jersey).

Stec et al., *J. Am. Chem. Soc* 106, 6077 (1984).

Iyer et al., *J. Am. Chem. Soc.* 112, 1253 (1990).

Iyer et al., *J. Org. Chem.* 55, 4693 (1990).

Storey et al., *Nucleic Acids Res.* 19, 4109 (1991).

Robertson et al., *J. Virology* 54, 651 (1985).

Harris et al., *J. Virology* 36, 659 (1980).

Rice et al., *Science* 229, 726 (1985).

Davison and Scott, *J. Gen. Virology* 67, 2279 (1986).

Richards et al., *Virology* 89, 395 (1978).

Miller and Purcell, *Proc. Natl. Acad. Sci.* USA 87, 2057 (1990).

Simmonds et al., *J. Gen. Virol.* 74, 661–668 (1993).

Collins, P., in *The Paramyxo Viruses*, Chapter 4, pp. 103–162 (D. Kingsbury, ed., 1991).

Campbell et al., *Nature* 311, 350 (1984).

Zurita et al., *Proc. Natl. Acad. .Sci* USA 84, 2340 (1987).

Stahl and Prusiner, *FASEB J.*, 5, 2799 (1991).

Sum et al., *J. Am. Chem. Soc. Perkin Trans. 1*, p. 3183 (1994).

Carey et al., *J. Am. Chem. Soc. Perkin Trans. 1*, p. 831 (1993).

Beaucage and Iyer, *Tetrahedron Lett.* 48, 2223 (1992).

Bentrude et al., *J. Am. Chem. Soc.* 111, 3981 (1989).

Iyer et al., *Bioorg. Med. Chem. Lett.* 4, 2471 (1994).

Agrawal and Sarin, *Advanced Drug Delivery Rev.* 6, 251 (1991).

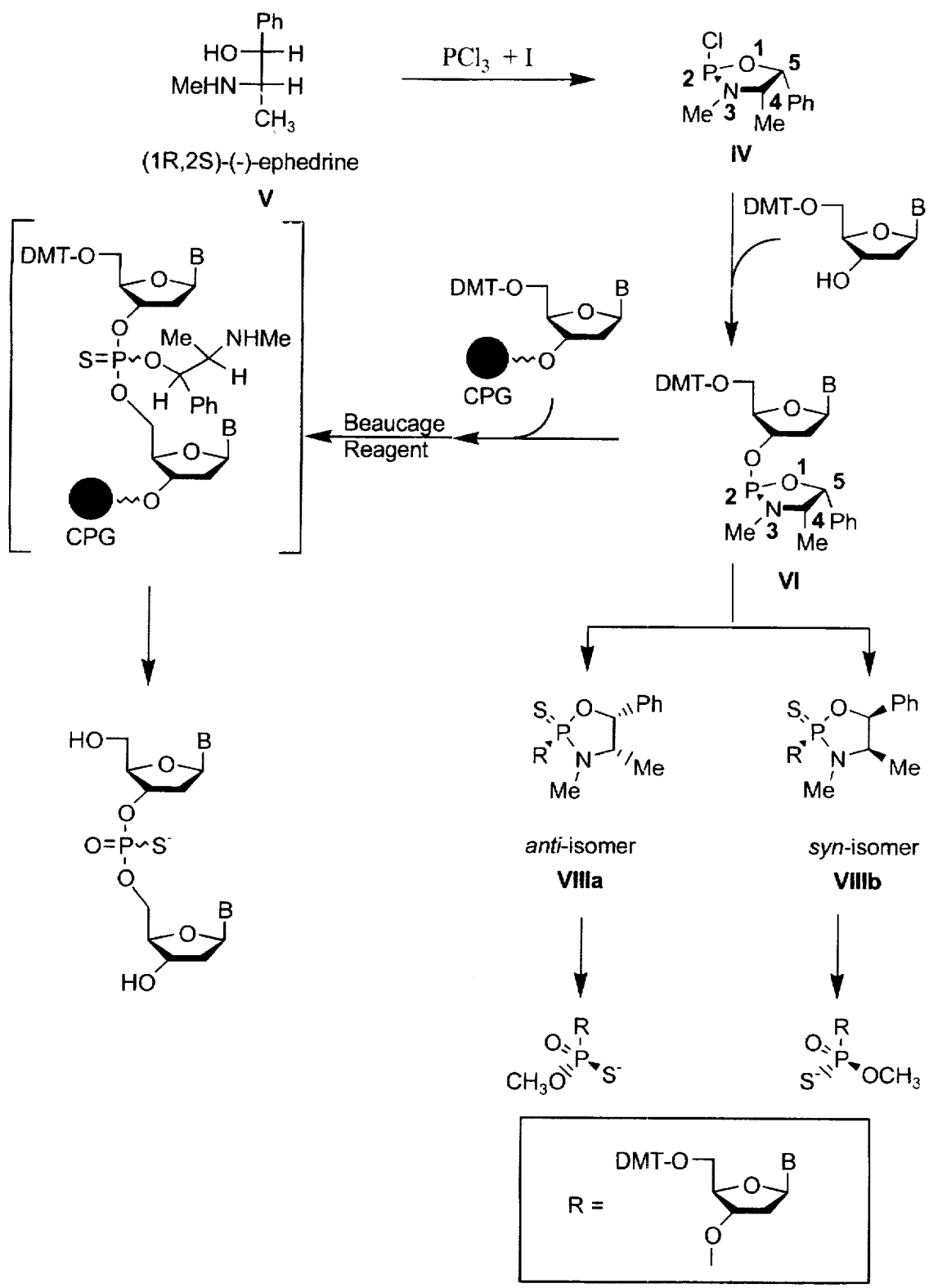

METHODS AND COMPOUNDS FOR THE STEREOSELECTIVE ENRICHMENT OF OLIGONUCLEOTIDE DIASTEREOMERS AND OLIGONUCLEOTIDES THEREBY PRODUCED

BACKGROUND OF THE INVENTION

1. Field of the Invention

This invention relates to methods for the chemical synthesis of oligonucleotides stereoselectively enriched in a particular diastereomer, compounds useful in the methods, and oligonucleotides thereby produced.

2. Description of the Prior Art

Since Zamecnik and Stephenson, *Proc. Natl. Acad Sci. USA* 75, 280–284 (1978), first demonstrated virus replication inhibition by synthetic oligonucleotides, there has been much interest in the use of antisense oligonucleotides as agents for the selective modulation of gene expression, both in vitro and in vivo. See, e.g., Agrawal, *Trends in Biotech.* 10, 152 (1992); Chang and Petit, *Prog. Biophys. Molec. Biol.* 58, 225 (1992); and Uhlmann and Peymann, *Chem. Rev.* 90, 543 (1990). Antisense oligonucleotides are constructed to be sufficiently complementary to a target nucleic acid to hybridize with the target under the conditions of interest and inhibit expression of the target. Antisense oligonucleotides may be designed to bind directly to DNA (the so-called "anti-gene" approach) or to viral RNA or mRNA. Id. Expression inhibition is believed to occur by interfering with transcription processing or translation, or inducement of target mRNA cleavage by RNase H.

Antisense oligonucleotides can be used as research tools in vitro to determine the biological function of genes and proteins. They provide an easily used alternative to the laborious method of gene mutation (e.g., deletion mutation) to selectively inhibit gene expression. The importance of this method is readily appreciated when one realizes that the elucidation of most known biological processes has been determined by deletion mutation.

Antisense oligonucleotides also may be used to treat a variety of pathogenic diseases by inhibiting gene expression of the pathogen in vivo. Oligonucleotide phosphorothioates (PS-oligos) have shown great therapeutic potential as antisense-mediated inhibitors of gene expression (Stein and Cheng, *Science* 261, 1004 (1993) and references therein) as evidenced by a number of ongoing clinical trials against AIDS and cancer. Agrawal and Tang, *Antisense Res. and Dev.* 2, 261 (1992) and references therein, and Bayever et al., *Antisense Res. Dev.* 3, 383 (1993). Various methods have been developed for the synthesis of oligonucleotides for such purposes. See generally, *Methods in Molecular Biology*, Vol 20: *Protocols for Oligonucleotides and Analogs* pp. 165–189 (S. Agrawal, Ed., Humana Press, 1993); *Oligonucleotides and Analogues: A Practical Approach*, pp. 87–108 (F. Eckstein, Ed., 1991); and Uhlmann and Peyman, supra. PS-oligos synthesized by these methods are mixtures of $2^n$ diastereomers, where n is the number of internucleotide phosphorothioates. To date only limited data is available on the comparative biophysical and biological properties of stereodefined phosphorothioates due to non-availability of sufficient quantities of completely "stereoregular" PS-oligos of sufficient length. Stec, *Angew-Chem. Int. Ed. Engl.* 33, 709 (1994) and references therein; Lesnikowski, *J Bioorg- Chem.*, 21, 127 (1993); Stec and Lesnikowski in *Methods in Molecular Biology*, Vol. 20, supra, pp. 285–313 and references cited therein; and Tang et al., *Nucleosides Nucleotides*, in press (1995). Enzymatic synthesis (Tang et al., supra) gives only $R_p$-phosphorothioates and is not as yet amenable to large-scale work.

The effects of different diastereomers on the efficacy of antisense oligonucleotides for gene modulation remain largely unknown. The potential impact of stereoselective synthesis to augment antisense oligonucleotide efficacy, however, is great. There is a need, therefore, for further research to increase knowledge in this area and to develop methods for large-scale synthesis of "stereoregular" PS-oligos. Concomitantly, there is a need for additional synthetic research tools to aid in this endeavor.

SUMMARY OF THE INVENTION

The present invention provides novel synthons and synthetic methods useful for the chemical synthesis of antisense oligonucleotides enriched in a particular diastereomer. The invention also provides oligonucleotides produced from these compounds by these methods. These oligonucleotides are useful inhibitors of nucleic acid expression.

In one aspect of the invention, we provide diastereomerically enriched monomer synthons having the structure:

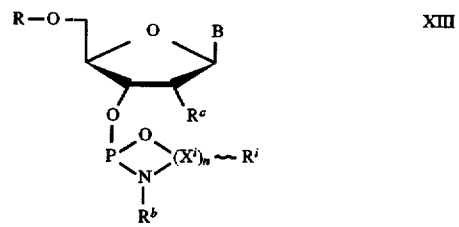

where B is any suitably protected purine or pyrimidine base or derivative thereof and each of the chiral $X^i$ have a well defined stereoconfiguration. These synthons as well as derivatives and analogs thereof are useful in the synthesis of diastereomerically pure oligonucleotides by the phosphoramidite method. They can be used as a substitute for the well-known β-cyanoethyl-protected phosphoramidate.

In a preferred embodiment, synthon XIII has the form:

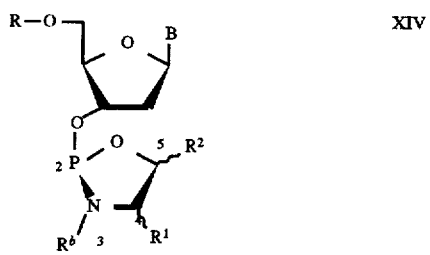

where chiral centers 4 and 5 can be, respectively, R and S, S and R, R and R, or S and S.

In a particularly preferred embodiment of this aspect of the invention, synthon XIII has the form:

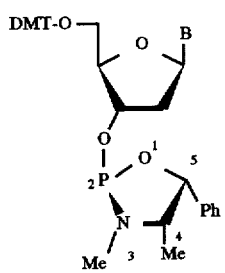
VI

In another aspect of the invention, a method of synthesizing the diastereomerically enriched monomer synthons XIII, XIV, and VI is provided. The method comprises contacting

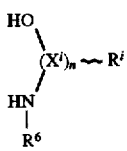
XVII to yield

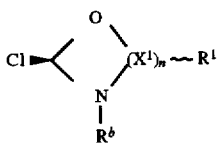
XVIII which, when contacted with a 5'-protected mononucleoside having an unprotected 3' hydroxyl, yields XIII.

In a preferred embodiment of this aspect of the invention, XVII takes the form:

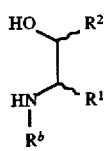
XIX and yields

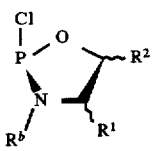
XX which can be reacted with a mononucleoside to yield XIV.

In a particularly preferred embodiment of this aspect of the invention, (1R, 2S)-(−)-ephedrine (V) with PCl₃ to yield the chlorophosphoramidite product:

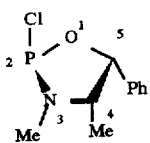
IV

The R_p isomer predominates (>95%). Contacting IV with a 5'-DMT-protected mononucleoside having a free 3' hydroxyl group yields the monomer synthon VI in high yield (84%).

Each of the foregoing reactions is stereoretentive. Thus, particular diastereomers of each of XIII, XIV, and VI can be obtained by starting with the appropriate stereoisomer of XVII, XIX, and V, respectively.

In another aspect of the invention, thiophosphoramidate monomer synthons enriched in a particular stereoisomer are provided. These compounds have the general structures:

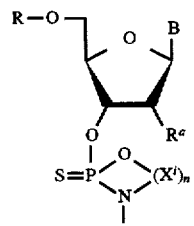
XV and

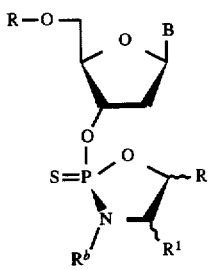
XVI

In a preferred embodiment of this aspect of the invention, thiophosphoramidate monomer synthons having syn-(VIIIb) and anti-(VIIIa) conformations are provided:

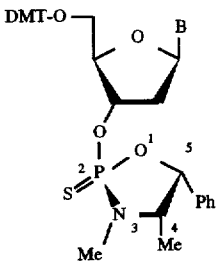
VIIIa anti-isomer

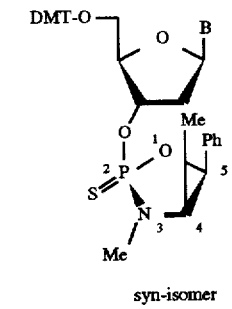
VIIIb syn-isomer

XV, XVI, VIIIa and VIIIb are all made by oxidatively thiolating the monomer synthon precursors XIII, XIV, and VI, respectively, with a sulfurizing agent such as the 3H-1,2-benzodithiole-3-one-1,1-dioxide reagent. The result is about 90% retention of configuration. The stereoisomers can be separated by flash chromatography.

In another aspect of the invention, oligonucleotides having one or more P-chiral centers predominantly in the S configuration and methods for their synthesis have been developed. In one embodiment of this aspect of the present invention, these oligonucleotides can be synthesized via the well-known phosphoramidate approach using XIII, XIV, or VI instead of the well known β-cyanoethyl phosphoramidite synthon. The intermediate phosphite linkage may be oxidized with, for example, I₂ and H₂O in THF to yield a phosphodiester linkage, or oxidatively thiolated with a sulfurizing agent, such as the Beaucage reagent, to yield a phosphorothioate linkage. Oligonucleotides synthesized according to this embodiment of the invention will have predominantly $S_p$ configuration (~60%) at each internucleotide linkage in which compound XIII, XIV, or VI was employed during synthesis.

In another embodiment of this aspect of the invention, one of XV, XVI, VIIIa or VIIb is contacted with a nascent oligonucleotide having a free 5' hydroxyl group. When either VIIIa or VIIb is used, the result is an oligonucleotide having a 5' phosphorothioate internucleotide linkage with an $R_p$:$S_p$ ratio of about 70:30 when VIIIa is used and 10:90 when VIIb is used. Similar results are obtained from compound XVI when $R^1$ and $R^2$ are both anti- or both syn- with respect to the nucleoside and compound XV when all of the $R^i$ are anti- or syn- with respect to the nucleoside.

As noted, each of the foregoing monomer synthons and oligonucleotides can be synthesized using the methods of the present invention to be in enantiomeric excess. One advantage of the methods of the present invention is that the stereochemistry of the precursors is maintained in the products, and, if the reactants are in enantiomeric excess, the products are predominantly in one stereoconfiguration.

Oligonucleotides according to the invention are useful for both in vitro and in vivo applications. For in vitro applications, the present oligonucleotides are useful as research tools in determining gene function by effecting gene modulation.

Oligonucleotides according to the invention are also useful for in vivo applications, such as the treatment of pathogen-caused diseases. Oligonucleotides according to the invention can be synthesized to have a sequence sufficiently complementary to a region of a nucleic acid essential for the growth, reproduction, and/or metabolism of the pathogen to inhibit expression of the nucleic acid under physiological conditions.

The foregoing merely summarizes certain aspects of the present invention and is not meant, nor should it be construed, to limit the invention in any way. All patents and other publications cited herein establish the state of the art and are hereby incorporated by reference in their entirety.

BRIEF DESCRIPTION OF THE DRAWINGS

FIG. 1 displays the synthetic pathway for making the compounds of the present invention.

DETAILED DESCRIPTION OF THE PREFERRED EMBODIMENTS

The present invention provides a structurally novel class of antisense oligonucleotides useful for modulation of nucleic acid expression in vitro and in vivo. The present invention also provides novel methods for synthesizing this class of oligonucleotides using new synthons.

In one aspect of the invention, we provide diastereomeric mononucleotide synthons enriched in one of the diastereomers and having the general structure:

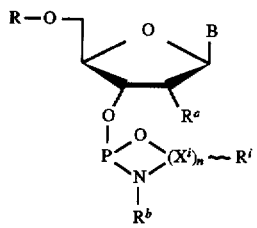

wherein $R^a$ and $R^b$, and each $R^i$ are independently H, $C_1$–$C_{20}$ alkyl, aryl, heterocyclic, $C_1$–$C_{20}$ alkoxy, R is a suitable protecting group, such as DMT, n is 1–3, i is 1-n, $X^i$ is C, O, S, or N, such that if n>1 the identity of each $X^i$ (i.e., each of $X^1$ ... $X^i$) is independent of the identity of every other $X^i$ and the identity of each substituent $R^i$ (i.e., $R^1$ ... $R^n$) is independent of every other $R^i$, each $R^i$ is covalently bound to the corresponding $X^i$ (e.g., $X^1$–$R^1$ ... $X^n$–$R^n$), the $X^i$ are arranged consecutively such that $X^1$ is bound to the N and $X^n$ is bound to the O, and B is any suitably protected, modified or unmodified, purine or pyrimidine base. As used herein, the term "aryl" means a polyaromatic-ring structure having from 1 to 5 linearly or angularly fused aromatic rings, such as phenyl and naphthyl. As used herein the term "heterocyclic" means a 5 or 6 membered ring having from 1 to 5 heteroatoms (i.e., N, S, or O) that may be located at any position within the ring. Furan and thiophene are examples of heterocyclic moieties encompassed by this definition. Compound XIII is synthesized according to the methods of the present invention (infra) to be predominantly in one stereoconfiguration.

The stereochemistry of the product XIII depends on the stereochemistry of the starting material. Synthesis of XIII from its precursor is accomplished in a stereoretentive manner, infra.

In a preferred embodiment of this aspect of the invention, $R^a$ is H, n is 2, and $X^1$ and $X^2$ are each C, which has the structure XIV:

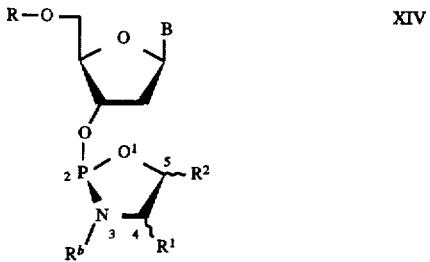

In this embodiment, the configurations at carbons 4 and 5 can be, respectively, R and S, S and R, R and R, or S and S, each of which can be obtained in pure form.

In a particularly preferred embodiment of this aspect of the present invention, n is 2, $X^1$ and $X^2$ are each C, $R^1$ is methyl, $R^2$ is phenyl, $R^a$ is H, $R^b$ is methyl, and the compound has the $R_p$ configuration as shown in structure VI:

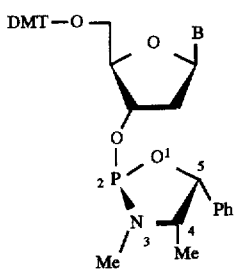

All of the four diastereomers of VI (in which carbons 4 and 5 are in the (R,S), (S,R), (R,R), and (S,S) configurations) can be made from one of the stereoisomers of precursor IV, infra.

Myriad suitable base protecting groups are known to those skilled in the art. E.g., Sonveaux in *Methods in Molecular Biology*, Vol. 26: *Protocols for Oligonucleotide Conjugates* pp. 1-72 (S. Agrawal, Ed., Humana Press (1994)) and references cited therein. Similarly, numerous modified bases are known to those skilled in the art. E.g., Meyer, *Methods in Molecular Biology*, v. 26, supra, pp. 73-92 and references cited therein. Synthons XIII, XIV, and VI and derivatives thereof are useful in the synthesis of oligonucleotides by the phosphoramidite method, as discussed more fully below. It can be used as a substitute for the well-known β-cyanoethyl-protected phosphoramidate:

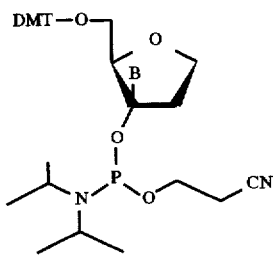

Furthermore, the synthetic protocol for incorporating XIII, XIV, and VI in a nascent oligonucleotide is the same as that for the β-cyanoethyl-protected phosphoramidates. E.g., Beaucage in *Methods in Molecular Biology*, Vol. 20, *Protocols for Oligonucleotides and Analogs*, supra, pp. 33-61 and references cited therein. For simplicity, as used herein the term "nascent oligonucleotide" means a solid support-bound nucleotide chain having at least one nucleotide.

In another aspect of the invention, a method of synthesizing the diastereomerically enriched monomer synthon XIII is provided. In this aspect of the invention PCl₃ is reacted with a compound of structure XVII:

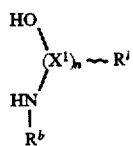

to yield

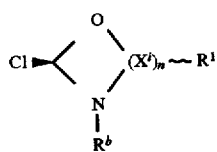

where each of X$^i$, R$^i$, R$^b$, and n are defined the same as described for compound XIII. XVIII is contacted with a 5'-protected mononucleoside having an unprotected 3'-hydroxyl to yield XIII. Compounds XIII and XVIII are obtained from their precursors (XVIII and XVII, respectively) a stereoretentive manner, i.e., the stereoconfiguration of the precursor is maintained in the reaction.

Compound XIV is obtained in a similar manner by contacting XIX

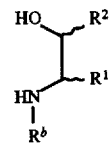

with PCl₃ to yield

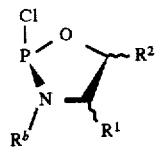

wherein each of R$^1$ and R$^2$ are the same as R$^i$ in compound XIII and R$^b$ is the same as in compound XIII. Compound XIV is obtained by contacting XX with a 5'-protected mononucleoside having an unprotected 3'-hydroxyl. As before, the reactions are stereoretentive, and the products of each reaction, XIV and XX, retain the same stereoconfiguration as their precursor, XX and XIX, respectively.

In a preferred embodiment of this aspect of the invention, a method of synthesizing the diastereomerically enriched monomer synthon VI is provided. The method comprises contacting (1R, 2S)-(-)-ephedrine (V) with PCl₃ at between −100° and 40° C. for between one and 40 hours. In a preferred embodiment, the two compounds are allowed to react in N-methyl morpholine and toluene at −78° C. for 3 hours and then at 22° C. for 12 hours. Other suitable solvents are benzene, tetrahydrofuran, ether, and dioxane. The result is about a 75% yield of the chlorophosphoramidite product:

The R$_p$ isomer predominates (>95%). Contacting IV with a 5'-DMT-protected mononucleoside having a free 3'-hydroxyl group yields the monomer synthon VI in high yield (84%). In a preferred embodiment, the mononucleoside and IV are allowed to react in ethyl ether and triethylamine as a scavenger of HCl liberated during the reaction. Other 10 scavengers such as pyridine and 2,6-lutidine can also be used. The reaction can be conducted at temperatures ranging from between −100 and 40° C. for between 1 and 40 hours. In a preferred embodiment, the mixture is allowed to react at −78° C. for 3 hours and then at 22° C. for 12 hours. Other suitable solvents such as benzene, tetrahydrofuran, ether, and dioxane can also be used. Compound IV is fairly stable, undergoing no apparent decomposition (as evaluated by ³¹P-NMR) after being stored at −5° C. for several days.

The other stereoisomers of ephedrine (1S,2R; 1S,2S; and 1R,2R) (V) are also commercially available and can be used in place of (1R ,2S)-(-)-ephedrine (V) to obtain the other diastereomers of IV:

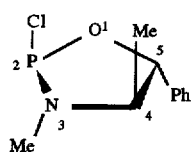

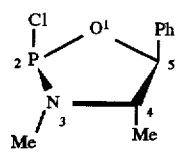

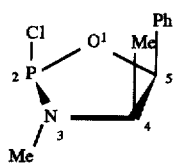

In another aspect of the invention, thiophosphoramidate monomer synthons enriched in a particular stereoisomer are provided. These compounds have the general structures:

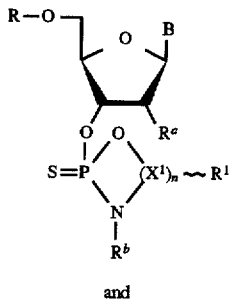

XV and

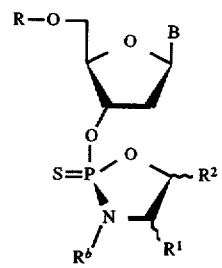

XVI wherein the definitions of B, R, R$^i$, R$^a$, R$^b$, R$^1$, R$^2$, X$^i$, i, and n are the same as described previously for compound XIII. Monomer synthons XV and XVI are obtained in the predominant configurational stereoisomer by stereoretentive oxidative thiolation of the phosphorous of compounds XIII and XIV, respectively. Oxidative thiolation of a particular stereoisomer of XIII or XIV (provided above) results in approximately 90% conversion to the corresponding thiophosphoramidate stereoisomer.

In a preferred embodiment of this aspect of the invention, the anti- isomer of synthon VIII is provided. The syn- (VIIIb) and anti- (VIIIA) forms of the synthon VIII according to this aspect of the invention have the following structures:

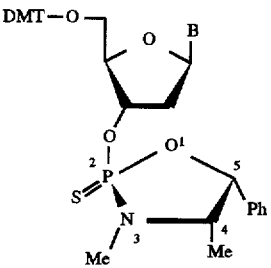

anti-isomer

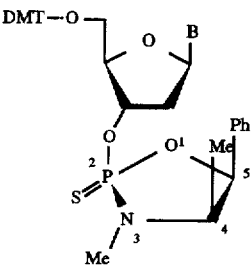

syn-isomer

VIIIa and VIIIb are made by oxidatively thiolating the monomer synthon VI. The result is a 90:10 anti:syn mixture.

Any suitable method of oxidative thiolation may be used, such as elemental sulfur. E.g., Stec et al., *J. Am. Chem. Soc.* 106, 6077 (1984). Preferably, the thiophosphoramidate monomer synthons are synthesized by contacting the phosphoramidite precursors with the Beaucage reagent, 3H-1,2-benzodithiol-3-one-1,1-dioxide:

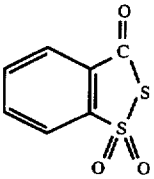

I according to the method of Iyer et al., *J. Am. Chem. Soc.* 112, 1253 (1990) and Iyer et al., *J. Org Chem.* 55, 4693 (1990). In a preferred embodiment, reagent I is used as a 2% solution in acetonitrile and the mixture is allowed to react for 30 seconds at about room temperature. All of the various diastereomers (e.g., VIIIa and VIIIb) are easily separated by conventional chromatography or crystallization.

In another aspect of the invention, oligonucleotides having from one to all nucleotide P-chiral centers independently predominantly in the S configuration and methods for synthesizing them are provided. As used herein, the term "predominantly" means more than half. In one embodiment of this aspect of the present invention, these oligonucleotides can be synthesized via the well-known phosphoramidate approach (e.g., Beaucage in *Methods in Molecular Biology*, Vol.20, *Protocols for Oligonucleotides and Analogs*, supra, pp. 33–61 and references cited therein) using XIII in place of XII. In a preferred embodiment of this aspect of the invention, XIV is used in place of XII. In a particularly preferred embodiment, VI is used.

In brief, a nascent oligonucleotide having a free 5' hydroxyl is contacted with XIV, XV, or VI in the presence of tetrazole. A phosphite linkage is thereby formed. The phosphite linkage may then be oxidized with, for example, I$_2$ and H$_2$O in THF to yield a phosphodiester linkage or oxidatively thiolated with I to yield a phosphorothioate linkage. Phosphorothioate oligonucleotides synthesized according to this embodiment of the invention have predominantly $S_p$ configuration (~60%) at each internucleotide linkage in which compound XIV, XV, or VI was employed during synthesis.

In another embodiment of this aspect of the invention, oligonucleotides having one or more phosphorothioate internucleotide linkages that are independently predominantly in the R or S configuration are provided. In this embodiment, one of the stereoisomers of XV or XVI is contacted with a nascent oligonucleotide having an unprotected 5' hydroxyl group. In a preferred embodiment, VIIIa or VIIIb is used, resulting in an oligonucleotide having a 5' phosphorothioate internucleotide linkage with an $R_p:S_p$ ratio of about 70:30 (starting with VIIIa) or 10:90 (starting with VIIIb). Similar results are obtained from compound XVI when $R^1$ and $R^2$ are both anti- or both syn- with respect to the nucleoside and compound XV when all of the $R^i$ are anti- or syn- with respect to the nucleoside.

The antisense oligonucleotides of the present invention may be designed to incorporate a number of additional features that have been demonstrated to increase efficacy. For example, they may be designed to be "self-stabilized," i.e., having a first region sufficiently complementary to a second region to allow for intramolecular hybridization, thereby rendering the oligonucleotide less susceptible to nucleolytic attack. Such oligonucleotides are described in PCT International Application Publication No. WO 94/01550.

Alternatively, the presently disclosed oligonucleotides may be designed to be "fold-back triplex forming," i.e., having a first region complementary to a target nucleic acid and a second region having a sequence that allows for triplex formation by Hoogsteen base pairing between it and the duplex formed by the first region and the target nucleic acid, as described in PCT International Application Publication No. WO 94/17091.

Oligonucleotides according to the invention are useful for both in vitro and in vivo applications. For in vitro applications, the present oligonucleotides are useful as research tools in determining gene function. Because they can be prepared to be complementary to a particular sequence, the present oligonucleotides can be used to selectively inhibit expression of a target gene. The present oligonucleotides thus provide an attractive and easily used alternative to the laborious method of gene inhibition by mutation (e.g., deletion mutation). The significance of this will be appreciated when one realizes that the elucidation of most biological pathways now known has been determined by deletion mutations.

Oligonucleotides according to the invention are also useful in standard hybridization assays.

The oligonucleotides of the present invention are also useful as therapeutic agents for diseases or physiological conditions involving expression of specific genes. Oligonucleotides useful for treating a disease or condition will have a nucleotide sequence sufficiently complementary to the target nucleic acid to bind to the target nucleic acid under physiological conditions. As used herein, the terms "complementary" and "sufficiently complementary" are used interchangeably and, when used to describe the sequence of an antisense oligonucleotide, mean that the oligonucleotide sequence is such that the oligonucleotide inhibits expression of the target nucleic acid under the conditions of interest (e.g., in vitro experimental conditions or physiological conditions). In general, oligonucleotides according to the invention will have a sequence complementary to a nucleic acid (e.g., a gene or mRNA) that is essential to a biological process. As elaborated more fully below, such processes include reproduction and metabolic processes of pathogens and other disease-causing infectious agents. Alternatively, the biological process can be a naturally occurring one whose inhibition is desirable, e.g., spermatogenesis in men and ovulation in women desiring contraception. The oligonucleotides of the invention can also be complementary to a gene or other nucleic acid whose expression causes or is involved in a diseased or otherwise abnormal state of the organism.

Because of their efficacy at gene modulation, the presently claimed oligonucleotides are also useful for treating diseases arising from genetic abnormalities that cause under-or over-expression of a gene. For diseases in which an abnormal gene is expressed or a normal gene is over-expressed, for example, the presently claimed oligonucleotides may be designed to target the abnormal or normal gene directly, or, in the alternative, to target the gene encoding the protein that promotes expression of the abnormal or normal gene. Conversely, where a normal gene is under-expressed, one may design an oligonucleotide that suppresses expression of a gene encoding a protein that suppresses expression of the normal gene.

In many cases the target nucleic acid sequence will be a viral nucleic acid sequence. The use of antisense oligonucleotides to inhibit various viruses is well known and has been reviewed in Agrawal, *Trends in Biotechnology* 10, 152 (1992). Viral nucleic acid sequences that hybridize to effective antisense oligonucleotides have been described for many viruses, including human immunodeficiency virus type I (U.S. Pat. No. 4,806,463), Herpes simplex virus (U.S. Pat. No. 4,689,320), Influenzavirus (U.S. Pat. No. 5,194, 428), and Human papilloma virus (Storey et al., *Nucleic Acids Res.* 12, 4109 (1991)). Sequences hybridizing to any of these nucleic acid sequences can be used, as can nucleotide sequences complementary to nucleic acid sequences from any other virus. Additional viruses that have known nucleic acid sequences against which an antisense oligonucleotide according to the invention can be prepared include, but are not limited to, Foot and Mouth Disease Virus (See Robertson et al., *J. Virology* 54, 651 (1985); Harris et al., *J. Virology* 36, 659 (1980)), Yellow Fever Virus (see Rice et al., *Science* 229, 726 (1985)), Varicella-Zoster Virus (see Davison and Scott, *J. Gen. Virology* 67, 2279 (1986), Cucumber Mosaic Virus (see Richards et al., *Virology* 89, 395 (1978)), Hepatitis B Virus (see Raney and McLachlen, in *Molecular Biology of Hepatitis B Virus* (CRC Press, 1991)), Hepatitis C Virus (see Miller and Purcell, *Proc. Natl. Acad. Sci. USA* 87, 2057 (1990); *Proc. Natl Acad. Sci. USA* 89, 4942 (1992); *J. General Virology* 74, 661 (1993)), and Respiratory Syncitial Virus (see Collins, in *The Paramyxo Viruses*, Chapter 4, pp. 103–162 (David W. Kingsbury, Ed., 1991)).

Alternatively, the oligonucleotides of the invention can have a nucleotide sequence complementary to a nucleic acid sequence of a pathogenic organism. The nucleic acid sequences of many pathogenic organisms have been described, including the malaria organism, *Plasmodium falciparum* and many pathogenic bacteria. Examples of pathogenic eukaryotes having known nucleic acid sequences against which oligonucleotides of the present can be prepared include, but are not limited to *Trypanosoma brucei gambiense* and *Leishmania* (see Campbell et al., *Nature* 311, 350 (1984)), and *Fasciola hepatica* (see Zurita et al., *Proc. Natl. Acad Sci. USA* 84, 2340 (1987)). Antifungal oligonucleotides can be prepared having a nucleotide sequence that is complementary to a nucleic acid sequence from, e.g., the chitin synthetase gene, and antibacterial oligonucleotides according to the invention can be prepared using, e.g., the alanine racemase gene.

In yet another embodiment, the oligonucleotides can have a nucleotide sequence complementary to a cellular gene or gene transcript, the abnormal expression or product of which results in a disease state. The nucleic acid sequences of several such cellular genes have been described, including prion protein (Stahl and Prusiner, FASEB J. 5, 2799 (1991)), the amyloid-like protein associated with Alzheimer's disease (PCT International Application Publication No. WO 95/09236), and various well-known oncogenes and proto-oncogenes, such as c-myb, c-myc, c-abl, and n-ras.

In addition, oligonucleotides that inhibit the synthesis of structural proteins or enzymes involved largely or exclusively in spermatogenesis, sperm motility, the binding of the sperm to the egg or any other step affecting sperm viability may be used as contraceptives for men. Similarly, contraceptives for women may be oligonucleotides that inhibit production of proteins or enzymes involved in ovulation, fertilization, implantation or in the biosynthesis of hormones involved in those processes. Hypertension can be controlled by oligonucleotides that suppress the synthesis of angiotensin converting enzyme or related enzymes in the renin/angiotensin system; platelet aggregation can be controlled by suppression of the synthesis of enzymes necessary for the synthesis of thromboxane A2 for use in myocardial and cerebral circulatory disorders, infarcts, arteriosclerosis, embolism and thrombosis; deposition of cholesterol in arterial wall can be inhibited by suppression of the synthesis of fatty acyl co-enzyme A: cholesterol acyl transferase in arteriosclerosis; inhibition of the synthesis of cholinephosphotransferase may be useful in hypolipidemia.

There are numerous neural disorders in which oligonucleotides of the present invention can be used to reduce or eliminate adverse effects of the disorder. For example, suppression of the synthesis of monoamine oxidase can be used in Parkinson's disease; suppression of catechol O-methyl transferase can be used to treat depression; and suppression of indole N-methyl transferase can be used in treating schizophrenia.

Suppression of selected enzymes in the arachidonic acid cascade (which leads to prostaglandins and leukotrienes) may be useful in the control of platelet aggregation, allergy, inflammation, pain and asthma. Suppression of the protein expressed by the multi-drug resistance (mdr) gene, which is responsible for development of resistance to a variety of anti-cancer drugs and is a major impediment in chemotherapy may prove to be beneficial in the treatment of cancer. Nucleotide sequences complementary to nucleic acid sequences from any of these genes can be used for the oligonucleotides according to the invention, as can be oligonucleotide sequences complementary to any other cellular gene or gene transcript, the abnormal expression or product of which results in a disease state.

Antisense regulation of gene expression in plant cells has been described in U.S. Pat. No. 5,107,065, and the antisense oligonucleotides of the invention can potentially be applied in this context as well.

Since the nucleotide sequence of the oligonucleotide can be adapted to form Watson-Crick base pairs with essentially any gene, the therapeutic spectrum of the oligonucleotides of the invention should be very broad. Still, certain diseases are of particular interest. For example, a variety of viral diseases may be treated by oligonucleotides having one or more S-triesterphosphorothioates internucleotide linkages, including AIDS, ARC, oral or genital herpes, papilloma warts, flu, foot and mouth disease, yellow fever, chicken pox, shingles, HTLV-leukemia, and hepatitis. Among fungal diseases treatable by oligonucleotides according to the invention are candidiasis, histoplasmosis, cryptococcocis, blastomycosis, aspergillosis, sporotrichosis, chromomycosis, dematophytosis and coccidioidomycosis. The method can also be used to treat rickettsial diseases (e.g., typhus, Rocky Mountain spotted fever), as well as sexually transmitted diseases caused by *Chlamydia trachomatis* or *Lymphogranuloma venereum*.

A variety of parasitic diseases can be treated by oligonucleotides of the present invention, including amebiasis, Chagas' disease, toxoplasmosis, pneumocystosis, giardiasis, cryptosporidiosis, trichomoniasis, and *Pneumocystis carini* pneumonia; also worm (helminthic diseases) such as ascariasis, filariasis, trichinosis, schistosomiasis and nematode or cestode infections. Malaria can be treated by oligonucleotides of the present invention, regardless of whether it is caused by *P. falciparum*, *P. vivax*, *P. orale*, or *P. malaria*. The infectious diseases identified above can all be treated with oligonucleotides according to the invention because the infectious agents and their gene sequences for these diseases are known, and, thus, oligonucleotides according to the invention can be prepared having a nucleotide sequence that hybridizes to a nucleic acid sequence that is an essential nucleic acid sequence for the propagation of the infectious agent, such as an essential gene. As used herein, an essential gene or nucleic acid is one that is required for a biological process and without which the biological process does not occur.

The following examples are provided for illustrative purposes only and are not intended, nor should they be construed, as limiting the invention in any way.

EXAMPLES

Unless otherwise stated, all chemicals recited in the following Examples were obtained from Aldrich of Milwaukee, Wis.

Example 1

Stereoselective Synthesis of a Mononucleotide Synthon

The chlorophosphoramidite, (2R,4S,5R)-2-chloro-3,4-dimethyl-5-phenyl- 1,3,2-oxazaphospholidine (IV) was obtained by mixing 8.14 g of 1R,2S-ephedrine (V) and 10.4 ml of N-methyl morpholine in 250 ml of toluene under argon and cooling to −78° C. 4.3 ml of $PCl_3$ in 10 ml of toluene was added over a period of 15 minutes. The mixture was kept at −78° C. for 1 hour and then allowed to warm to room temperature over a period of 16 hours. The insoluble salt precipitate was filtered under argon. The precipitate was washed with 3×25 ml of toluene. The combined washings and filtrate were concentrated in vacuo in a rotary evaporator to remove toluene. Vacuum distillation of the residue gave a colorless liqued boiling at 0.1 mm Hg at 95° C. to give ca. 9 g (80% yield) of the product. This procedure is similar to that described previously. Sun et al., *J. Chem. Soc. Perkin Trans.* I p. 3183 (1994) and references therein and Carey et al., *J. Chem. Soc. Perkin Trans.* I, p. 831 (1993).

$^{31}$P-NMR examination of the resulting crude reaction mixture revealed the presence of- a predominant isomer (>95%) at δ169.4 ppm and a minor component (<5%) at δ161 ppm. Upon vacuum distillation of the reaction mixture (95°–97° C. at 0.1 mm Hg), a colorless liquid was obtained, which solidified to a white crystalline mass upon cooling to −78° C. (isolated yields of 75%). Carey et al., supra, reported a b.p. of 160° C. at 0.1 mm Hg. NMR analysis gave the following results: $^{31}$P-NMR (CDCl$_3$) (TMP external standard) δ169.1 ppm; $^1$H-NMR (CDCl$_3$) δ(ppm) 0.71 (3H, d, J=6.3 Hz), 2.69 (3H, d, $^3J_{P-H}$=15.1 Hz, N—CH$_3$), 3.63 (1H, ddq, J=1.3, 5.5, $^3J_{P-H}$=7.6 Hz, H-4), 5.85 (1H, dd, j=5.5 Hz, $^3J_{P-H}$~1.2 Hz), 7.15 (5H, m, -Ph). These spectral features are in agreement with values reported by Sun et al. and Carey et al., supra, and lead to the assignment of structure IV as being the R isomer in which the chlorine atom is disposed trans relative to the C-Ph and C-Me substituents in the phospholidine ring. IV could be stored as a solid in a desiccator at −5° C. for several days with no apparent decomposition (as evaluated by $^{31}$P-NMR). Upon addition of water to IV, the H-phosphonate VII was obtained as a mixture of diastereomers ($R_p$:$S_p$, 55:45 $^{31}$P-NMR).

2.16 g of 5'-O-dimethoxytrityl thymidine was dissolved in a mixture of anhydrous ether (20 ml) and anhydrous triethylamine (5 ml). The solution was added gradually (10 min) to 1.2 g of the chlorophosphoamidite (IV) at room temperature and the solution stirred at room temperature for 6 hours. The reaction mixture was poured into 200 ml of ice-cold water. It was then extracted with ethylacetate (3×200 ml). The combined organic layer was washed with water. The organic layer was evaporated to dryness to give 3 g (84% yield) of VI as a white foamy material.

Synthesis of XIII and XIV is conducted according to the same protocol.

The $^{31}$P-NMR spectrum of VI has a signal at δ140 ppm, corresponding to a single P-epimer. In analogy with substitution reactions of VI involving carbon-, oxygen-, and nitrogen-based nucleophiles (Sun et al. and Carey et al., supra), which gave substitution products with overall retention of configuration, VI can be formulated as having the structure with $R_p$ configuration (FIG. 1). This hitherto unreported nucleoside phosphoramidite VI is a white solid and is stable when stored dry at 0°–5° C. The NMR and mass spectral features of VI are as follows: $^{31}$P-NMR (CDCl$_3$) (TMP ext. standard) δ169 ppm; $^1$H-NMR (CDCl$_3$) δ(ppm) 0.61 (3H, d, J=6.5 Hz), 1.41 (3H, s, T—CH )$_3$ 2.42 (2H, m, H-2'), 2.63 (3H, d, $^3J_{P-H}$=12 Hz, N—CH$_3$), 3.37 (1H, dd, J=10.6, 2.6 Hz, H-5'), 3.46 (1H, dd, J=10.6, 2.6 Hz, H-5'), 3.52 (1H, ddq, J=6.9, 6.5 Hz, $^3J_{P-H}$=2.4 Hz, H-4), 3.76 (6H, s, —OCH$_3$), 4.08 (1H, m, H-4'), 4.91 (1H, m, H-3'), 5.56 (1H, dd, J=6.9 Hz, $^3J_{P-H(5)}$=1.84 Hz, H-5), 6.41(1H, dd, J=6.7, 6.7 Hz, H-1'), 6.85 (4H, m, —Ph), 7.25 (14H, m, —Ph), −7.6 (1H, s, H-6), 9.1 (1H, S. —NH). FAB-MS (m/z)=736 (M—H), C$_4$,H$_{44}$N$_3$O$_8$P.

Oxidative sulfurization of the phosphoramidite VI with thiolsulfonate I (R.I. Chemicals, Costa Mesa, Calif.) according to Iyer et al., J. Am. Chem. Soc. 112, 1253 (1990), and Iyer et al., J. Org. Chem. 55, 4693 (1990) gave the thiophosphoramidates VIIIa: VIIIb (90:10, 81% yield) (isomer ratio based on $^{31}$P-NMR. The NMR and mass spectral features were as follows: VIIIa, $^{31}$P-NMR (CDCl$_3$) δ(ppm) 79.0; $^1$H-NMR (CDCl$_3$) δ(ppm) 0.78 (3H, d, J=6.6 Hz, —CH$_3$) 1.41 (3H, s, T—CH3) 2.55 (2H, m, H-2'), 2.70 (3H, d, $^3J_{P-H}$=12.5 Hz, —NCH$_3$), 3.36 (1H, dd, J=10.5, 2.3 Hz, H-5'), 3.56 (1H, dd, J=10.5, 2.2 Hz, H-5') 3.76 (1H, ddq, J=6.6, 6.1 $^3J_{P-H}$=12.3 Hz, H-4), 3.78 (6H, s, —OCH$_3$), 4.28 (1H, m, H-4'), 5.57 (1H, m, H-3'), 5.62 (1H, dd, J=6.1 Hz, $^3J_{P-H(5)}$=2.8 Hz, H-5), 6.48 (1H, dd, J=9.0, 5.6 Hz, H-1'), 6.85 (4H, m, —Ph), 7.26 (14H, m, —Ph), 7.62 (1H, s, H-6) 8.90 (1H, s, —NH). FAB-MS (m/z) 769, C$_{41}$H$_{44}$N$_3$O$_8$PS.

The predominant isomer, VIIIA (which is easily separated from VIIIb by flash chromatography), has been assigned the configuration indicated in FIG. 1. The assignment of configurations for VIIa and VIIIb is based on the generally accepted notion that P(III) oxidations proceed with high stereoselectivity and with overall retention of configuration. E.g., Beaucage and Iyer, Tetrahedron 48, 2223 (1992), and Bentrude et al., J. Am. Chem. Soc. 111, 3981 (1989).

Example 2

Synthesis of Nucleotide Dimers Using Diastereomerically Enriched Monomer Synthons Having obtained the nucleoside phosphoramidite VI in preparative-scale reactions, the stage was set for its use in solid-phase coupling with CPG-bound nucleoside. Thus, contacting a solution of VI in acetonitrile with CPG-T (10 mmol) for a period of two minutes in the presence of tetrazole as an activator followed by oxidation with the thiolsulfonate I resulted in efficient formation of the product IX with a coupling efficiency of greater than 95% (as evaluated by "trityl yields"). Iyer et al., J. Am. Chem. Soc., supra, and Iyer et al., J Org. Chem., supra. Following synthesis, the CPG-bound product was heated with aqueous ammonium hydroxide (28%, 55° C., 1 hr). Examination of the products by reverse-phase HPLC revealed that the dinucleoside phosphorothioate X had been formed as a mixture of diastereomers ($R_p$:$S_p$, 40:60). Interestingly, the commonly used cyanoethylphosphate deprotection strategy (28% aq. NH$_4$OH, 55° C.) was found to be sufficient to cleave the chiral phosphate appendage in IX and generate the phosphorothioate X. The lack of high stereoselectivity in the formation of X is consistent with other reports wherein epimerization of the phosphorous center (in the case of stereoisomerically pure phosphoramidites) is observed when acidic type activators, e.g., tetrazole, are used in conjunction with phosphoramidite methodology in the synthesis of deoxyribonucleoside phosphorothioates. Stec, supra, and Beaucage, supra.

Example 3

Synthesis and Purification of Oligonucleotides

Oligonucleotides are synthesized on a 1 mmol scale following the standard protocol by using an automated synthesizer (e.g., Millipore 8700 DNA Synthesizer, Bedford, Mass.). Where a predominantly $R_p$ configuration is desired, the phosphoramidite VI is used by dissolving it in dry acetonitrile at a concentration of 50 mg/ml. For phosphorothioate oligonucleotides, the iodine oxidation step is replaced by sulfurization with 3H-1,2-benzodithiol-3-one-1,1-dioxide (Beaucage reagent). Iyer et al., J. Org. Chem. 55, 4693 (1990). Two-hour treatment with ammonium hydroxide at room temperature is carried out to cleave the oligomer from the support and to deprotect nucleoside bases. Oligonucleotides are purified by reverse-phase HPLC and/or PAGE, and desalted by using C-1 SEP-PAK cartridges.

Example 4

Stereoselective Synthesis of a Mononucleotide Phosphorothioate

Treatment of VIIIa and VIIIb with sodium methoxide in methanol at ambient temperature overnight followed by heating with NH$_4$OH (28% NH$_4$OH for 1–2 hr at 55° C. gave the phosphorothioate:

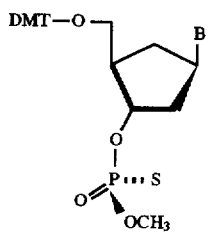

XI in 90% yield with moderate to high stereoselectivity (as monitored by $^{31}$P-NMR and HPLC). The $R_p$:$S_p$ ratio of XI obtained from VIIIa was 70:30, whereas the ratio of isomers obtained from VIIIb was 10:90. Configurations were assigned using the criteria reported for dinucleoside phosphorothioates by Iyer et al., *Bioorg. Med. Chem. Lett.* 4, 2471 (1994).

Example 5

Stereospecific Phosphorothioate Synthesis

Diazabicyclononane (DBU) (296 mg, 1.95 mmol) is dissolved in anhydrous THF (1.5 ml) and added to 3'-O-t-butyl dimethylsilyl thymidine (46 mg, 0.129 mmol) at 0° C. for 20 minutes. This solution is added slowly to the solution of VIIIa (50 mg, 0.065 mmol) and the contents stirred for 30 minutes at room temperature. The reaction mixture is allowed to warm to room temperature and stirred for 12 h. The solution is evaporated to remove solvent and treated with ammonium hydroxide (28%, 1 ml) and heated for 4 h at 55° C. The solution is evaporated to dryness. Chromatographic purification affords 45 mg (70% yield) of 5'-O-DMT-3'-O-TBDMS TT dimer with $R_p$:$S_p$ ratio of 70:30.

Example 6

Cellular Uptake

Cell culture

Human T cell and leukemia cell line H9 are used in this study. They are cultured in RPMI media supplemented with 10% fetal bovine serum (heat inactivated to 56° C. for 30 minutes to inactivate the nucleases), 2 mM glutamine, 100 ml streptomycin, 100 U/ml penicillin and $6\times10^{-5}$M of 2-mercaptoethanol in an air incubator (37° C., humidified by 5% $CO_2$-95% $O_2$).

Fluorescein labeling of oligonucleotides Fluorescein is conjugated to the 5' end of the oligonucleotides by either an automated DNA synthesizer or by a manual procedure using a "FLUORESCEIN-ON" phosphoramidite. The efficiency of fluorescein labeling is determined by using a spectrofluorometer (excitation 488 nm, emission 520 nm).

Cell uptake

The concentrations of the fluorescein labeled and unlabelled oligonucleotides in the samples are measured by a spectrofluorometer and UV spectroscopy and adjusted to be the same by adding the corresponding unlabelled oligonucleotides. Labelled oligonucleotides (0.2 OD/100 ml) are added to the cells ($5\times10^6$ cells/ml, 0.5 ml) and set to culture. After 4 hours of culture, aliquots of cell culture mixtures are removed, washed, and resuspended in Hank's balanced salt solution (HBSS) supplemented with 0.1% BSA and 0.1% sodium azide. Propidium iodide (final concentration 10 μl/ml) is used to distinguish viable cells from dead cells. Flow cytometric data on 5,000 viable cell is acquired in list mode on Epics XL (Coulter, Hialeah, Fla.), and data are analyzed by Epics XL (version 1.5 software) after gating on living cells by forward scatter versus side scatter and propidium iodide staining.

The results demonstrate that oligonucleotides according to the invention are taken up by cells.

Example 7

Inhibition of HIV-1 Replication

The following assays are used to measure the ability of the oligonucleotide of the invention to inhibit HIV-1 replication.

Syncytia Assay

The ability of the oligonucleotides of the invention to inhibit HIV-1 replication, and thus syncytia formation, in tissue culture is tested in T cell cultures according to the method of Agrawal and Sarin, *Advanced Drug Delivery Rev.* 6, 251 (1991). Briefly, CEM cells are infected with HIV-1 virions (0.01–0.1 $TCID_{50}$/cell) for one hour at 37° C. After one hour unadsorbed virions are washed and the infected cells are divided among walls of 24 well plates. To the infected cells, an appropriate concentration (from stock solution) of oligonucleotide is added to obtain the required concentration in 2 ml medium. The cells are then cultured for three days. At the end of three days, infected cells are examined visually for syncytium formation or stained with trypan blue or CTT for cytopathic effect determination.

The results demonstrate that oligonucleotides according to the invention inhibit syncitia formation. ps p24 Expression Assay HIV expression can be determined by measuring the level of viral protein p24 expression in CEM cells essentially as described by Agrawal and Sarin, supra. Briefly, cells are pelleted and then resuspended in phosphate saline at a concentration of about $10^6$/ml. The cells are spotted on toxoplasmosis slides, air dried, and fixed in methanol/acetone (1:1) for 15 min at room temperature (RT). The slides are next incubated with 10% normal goat serum at RT for 30 min and washed with phosphate buffered saline (PBS). Anti-p24 monoclonal antibody is added to each well, and the slides are incubated in a humid chamber at 37° C. The slides are labelled with goat anti-mouse IgG for 30 min and then washed in PBS overnight. The percentage of cells fluorescing in oligonucleotide-treated and untreated cells is compared.

The results demonstrate that oligonucleotides according to the invention substantially and significantly reduce p24 expression.

Cytopathic Effect (CPE)

HIV-induced cytopathic effect is determined by measuring the decrease in the number of viable cells after infection. The cells are counted by adding MTT or trypan blue dye to the cells and determining how many cells (dead) take up the dye. The assay is done in triplicate.

The results demonstrate that oligonucleotides according to the invention will reduce the viral cytopathic effect.

Reverse Transcriptase Assay

This assay is performed essentially as described in Agrawal and Sarin, supra. Supernatants from virus-infected cultures in the presence and absence of oligonucleotide are collected and virus particles precipitated with poly (ethyleneglycol). The virus pellet is suspended in 300 μl of buffer containing 50 mM Tris-HCl (pH 6.8), 5 mM dithiothreitol (DTT), 250 mM KCl, and 25% Triton X-100. Reverse transcriptase activity in the solubilized pellet is assayed in a 50 μl reaction mixture containing 50 mM Tris-HCl (pH 7.8), 5 mM DTT, 100 mM KCl, 0.01% Triton X-100, 5 μg dt15.rAn as template primer, 10 mM $MgCl_2$, 15 μM [$^3$H]dTTP (15 Ci/mmol), and 10 μl of the disrupted virus suspension. After incubation for 1 hr at 37° C. and subsequent addition of 50 μg yeast tRNA, the incorporation into the cold trichloroacetic acid-insoluble DNA fraction is assayed by counting in a β scintillation counter.

The results demonstrate that oligonucleotides according to the invention inhibit reverse transcriptase.

We claim:

1. A mononucleotide synthon having the structure:

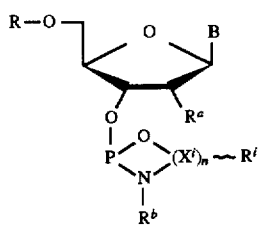

XIII wherein $R^1$, $R^b$ and each $R^i$ are independently H, $C_1$–$C_{20}$ alkyl, aryl, heterocyclic, or $C_1$–$C_{20}$ alkoxy, R is a protecting group, n is 1, 2, or 3, i is 1 to 3, each $X^i$ is C, O, S, or N provided that if n is 3 then (a) $X^2$ is optionally O, S or N, (b) $X^1$ and $X^3$ are C, and (c) there is no $R^2$ when $X^2$ is O or S.

each $R^i$ is covalently bound to the corresponding $X^i$, the $X^i$ are arranged consecutively such that the first of the $X^i$, $X^1$, is bound to the N and the last of the $X^i$, $X^n$, is bound to the ring O to form an n+3 membered ring and each chiral $X^i$ is predominantly in a single stereoconfiguration, and B is any protected, modified or unmodified, purine or pyrimidine base, provided that not all $R^i$ are H.

2. A mononucleotide synthon according to claim 1 having the structure:

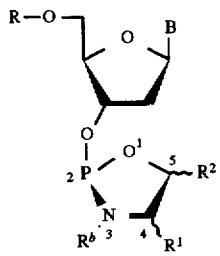

XIV wherein $R^1$ and $R^2$ are $R^i$ for i=1 and i=2, respectively.

3. A mononucleotide synthon according to claim 2 having the structure:

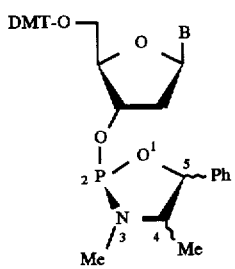

4. A mononucleotide synthon according to claim 3 having the structure and stereoconfiguration:

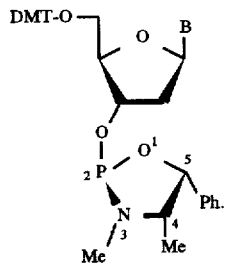

VI

5. A mononucleotide synthon having the structure:

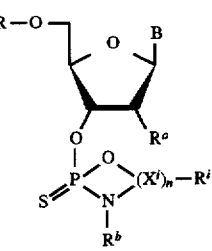

XV wherein $R^a$ and $R^b$ and each $R^i$ are independently H, $C_1$–$C_{20}$ alkyl, aryl, heterocyclic, or $C_1$–$C_{20}$ alkoxy.

R is a protecting group, n is 1, 2, or 3, i is 1 to 3, each $X^i$ is C, O, S, or N provided that if n is 3 then (a) $X^2$ is optionally O, S or N, (b) $X^1$ and $X^3$ are C, and (c) there is no $R^2$ when $X^2$ is O or S each $R^i$ is covalently bound to the corresponding $X^i$, the $X^i$ are arranged consecutively such that the first of the $X^i$, $X^1$, is bound to the N and the last of the $X^i$, $X^n$, is bound to the ring O to form an n+3 membered ring and each chiral $X^i$ is predominantly in a single stereoconfiguration, and B is any protected, modified or unmodified, purine or pyrimidine base provided that not all $R^i$ are H.

6. A mononucleotide synthon according to claim 5 having the structure:

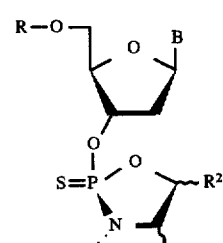

XVI wherein $R^1$ and $R^2$ are $R^i$ for i=1 and i=2, respectively.

7. A mononucleotide synthon according to claim 6 having the structure and configuration:

8. A mononucleotide synthon according to claim 6 having the structure and configuration:

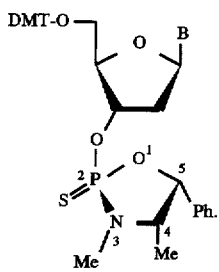 VIIIa

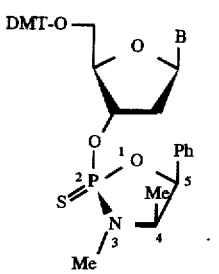 VIIIb

9. A method of synthesizing a mononucleotide synthon according to claim 1 comprising contacting a compound of structure:

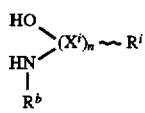 XVII with PCl₃ to yield

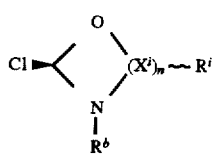 XVIII and then contacting XVIII with a 5'-protected mononucleoside having an unprotected 3'-hydroxyl.

10. A method of synthesizing the mononucleotide synthon of claim 2 comprising contacting a compound having structure:

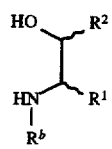 XIX with PCl₃ to yield

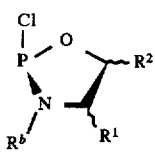 XX and then contacting XX with a 5'-protected mononucleoside having an unprotected 3'-hydroxyl.

11. A method of synthesizing the compound according to claim 3 comprising contacting ephedrine with PCl₃ to yield the chlorophosphoramidite:

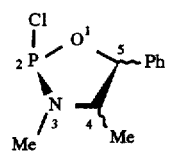

and then contacting the chlorophosphoramidite with a 5'-protected mononucleoside having an unprotected 3'-hydroxyl.

12. A method of synthesizing the compound according to claim 4 comprising contacting (1R,2S)-(−)-ephedrine with PCl₃ to yield the chlorophosphoramidite:

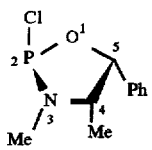 IV and then contacting IV with a 5'-protected mononucleoside having an unprotected 3'-hydroxyl.

13. A method of synthesizing the compound according to claim 5, comprising contacting compound XIII:

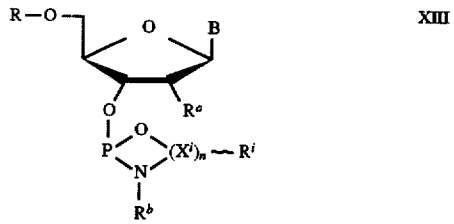 XIII with an oxidative thiolating agent.

14. A method according to claim 13, wherein the oxidative thiolation agent is 3H-1,2-benzodithiol-3-one- 1,1-dioxide.

15. A method of synthesizing the compound according to claim 6, comprising contacting compound XIV:

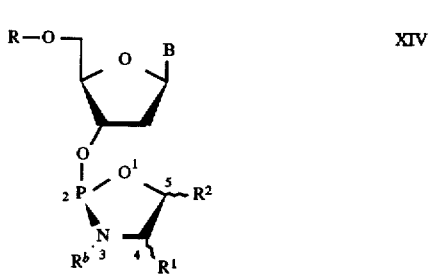 XIV with an oxidative thiolating agent.

16. A method according to claim 15, wherein the oxidative thiolation agent is 3H-1,2-benzodithiol-3-one-1,1-dioxide.

17. A method of synthesizing the compound according to claim 7, comprising contacting compound VI;

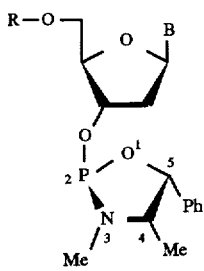

with an oxidative thiolating agent.

18. A method according to claim 17, wherein the oxidative thiolation agent is 3H-1,2-benzodithiol-3-one-1,11-dioxide.

19. A method of synthesizing an oligonucleotide having from one to all nucleotide P-chiral centers independently predominantly in the S configuration, comprising contacting a nascent oligonucleotide having a free 5'-hydroxyl with compound XIV having the structural formula:

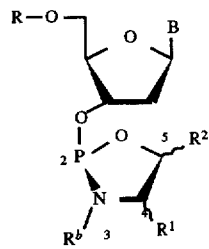

wherein:

$R^b$, $R^1$, and $R^2$ are independently H, $C_1$–$C_{20}$ alkyl, aryl, heterocyclic, or $C_1$–$C_{20}$ alkoxy, R is a protecting group, B is any protected, modified or unmodified, purine or pyrimidine base, and each chiral carbon of the phosphoramidite ring is predominantly in a single stereoconfiguration, provided that $R^1$ and $R^2$ are not both H.

20. A method of synthesizing an oligonucleotide having from one to all nucleotide P-chiral centers independently predominantly in the S configuration, comprising contacting a nascent oligonucleotide having a free 5'-hydroxyl with compound XV having structural formula:

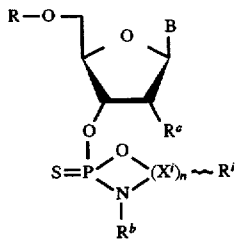

wherein $R^a$, $R^b$ and each $R^i$ are independently H, $C_1$–$C_{20}$ alkyl, aryl, heterocyclic, or $C_1$–$C_{20}$ alkoxy, R is a protecting group, n is 1, 2, or 3, i is 1 to 3, each $X^i$ is independently C, O, S, or N, provided that if n is 3 then (a) $X^2$ is optionally O, S or N, (b) $X^1$ and $X^3$ are C, and (c) there is no $R^2$ when $X^2$ is O or S, each $R^i$ is covalently bound to the corresponding $X^i$, the $X^i$ are arranged consecutively such that the first of the $X^i$, $X^1$, is bound to the N and the last of the $X^i$, $X^n$, is bound to the ring O to form a n+3 membered ring and each chiral $X^i$ is predominantly in a single stereoconfiguration, and B is any protected, modified or unmodified, purine or pyrimidine base, provided that not all $R^i$ are H.

21. A method of synthesizing an oligonucleotide having from one to all nucleotide P-chiral centers independently predominantly in the S configuration, comprising contacting a nascent oligonucleotide having a free 5'-hydroxyl with compound VI having structural formula:

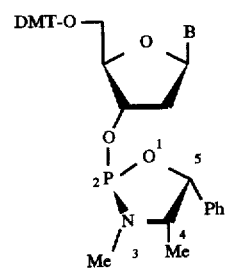

22. A method of synthesizing an oligonucleotide having from one to all phosphorothioate internucleotide linkages independently predominantly in the R or S configuration, comprising contacting a nascent oligonucleotide having a free 5'-hydroxyl with compound XV having structural formula:

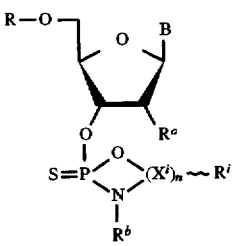

wherein $R^a$, $R^b$ and each $R^i$ are independently H, $C_1$–$C_{20}$ alkyl, aryl, heterocyclic, or $C_1$–$C_{20}$ alkoxy, R is a protecting group, n is 1, 2, or 3, i is 1 to 3, each $X^i$ is independently C, O, S, or N, provided that if n is 3 then (a) $X^2$ is optionally O, S or N, (b) $X^1$ and $X^3$ are C, and (c) there is no $R^2$ when $X^2$ is O or S, each $R^i$ is covalently bound to the corresponding $X^i$, the $X^i$ are arranged consecutively such that the first of the $X^i$, $X^1$, is bound to the N and the last of the $X^i$, $X^n$, is bound to the ring O to form a n+3 membered ring and each chiral $X^i$ is predominantly in a single stereoconfiguration, and B is any protected, modified or unmodified, purine or pyrimidine base, provided that not all $R^i$ are H.

23. A method of synthesizing an oligonucleotide having from one to all nucleotide P-chiral centers independently predominantly in the S configuration, comprising contacting a nascent oligonucleotide having a free 5-hydroxyl with compound XVI

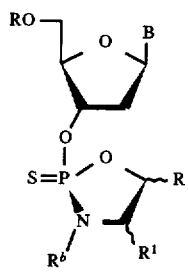

XVI wherein:

$R^b$, $R^1$, and $R^2$ are independently H, $C_1$–$C_{20}$ alkyl, aryl, heterocyclic, or $C_1$–$C_{20}$ alkoxy, R is a protecting group, B is any protected, modified or unmodified, purine or pyrimidine base, and each chiral carbon of the phosphoramidite ring is predominantly in a single stereoconfiguration, provided that $R^1$ and $R^2$ are not both H.

24. A method of synthesizing an oligonucleotide having from one to all nucleotide P-chiral centers independently predominating in the S configuration, comprising contacting a nascent oligonucleotide having a free 5'-hydroxyl with compound VIIIa or VIIIb having structural formulas:

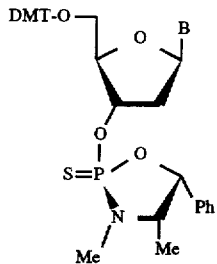

VIIa

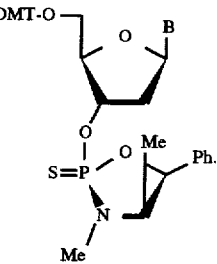

VIIb

* * * * *

UNITED STATES PATENT AND TRADEMARK OFFICE
CERTIFICATE OF CORRECTION

PATENT NO. : 5,750,674
DATED : May 12, 1998
INVENTOR(S) : Iyer et al.

It is certified that error appears in the above-identified patent and that said Letters Patent is hereby corrected as shown below:

Column 19,
Line 19, please change "$R^1$" to read -- $R^a$ --.

Signed and Sealed this

Ninth Day of July, 2002

Attest:

Attesting Officer

JAMES E. ROGAN
Director of the United States Patent and Trademark Office